(12) United States Patent
Bathe et al.

(10) Patent No.: US 6,509,475 B1
(45) Date of Patent: Jan. 21, 2003

(54) METHOD FOR PRODUCING 3-ALKANOYLINDOLES AND 3-ALKYLINDOLES

(75) Inventors: Andreas Bathe, Darmstadt (DE); Herbert Tilly, Pfungstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/857,793

(22) PCT Filed: Dec. 1, 1999

(86) PCT No.: PCT/EP99/09334

§ 371 (c)(1), (2), (4) Date: Jun. 11, 2001

(87) PCT Pub. No.: WO00/35872

PCT Pub. Date: Jun. 22, 2000

(30) Foreign Application Priority Data

Dec. 17, 1998 (DE) .......................... 198 58 340

(51) Int. Cl.$^7$ ............................................. C07D 209/04
(52) U.S. Cl. ........................................ 548/491
(58) Field of Search ......................... 548/491

(56) References Cited

U.S. PATENT DOCUMENTS

| | | | | |
|---|---|---|---|---|
| 5,128,482 A | * | 7/1992 | Olivier et al. | 548/494 |
| 5,157,122 A | * | 10/1992 | Hughes et al. | 546/176 |
| 5,290,946 A | * | 3/1994 | Lee et al. | 548/502 |

OTHER PUBLICATIONS

H Boettcher, R.Gericke: "Synthese von 3–[4–(1,2,3, 6–Tetrahydro–4–phenyl–1–pyridy 1)butyl]–5–indolcarbonsaeure, eine blutdrucksenkende Verbindung mit neuartigem wirkprinzip" Liebiegs Ann. Chem., 1988, Seiten 749–752, XP000882712 in der Anmeldung erwaehnt.

Snider, Barry B. et al: "Use of ethylaluminum dichloride as a catalyst for the Friedel—Crafts acylation of alkenes" J. Org. Chem., Bd. 47, Nr. 27, 1982, Seiten 5393–5395, XP000881554.

Eisch, John J. et al: "Reductive deoxygenation of ketones and secondary alcohols by organoaluminum Lewis acids" J. Org. Chem., Bd. 57, Nr. 7, 1992, Seiten 2143–2147, XP000881555.

Atul Agarwal et al.: "A new synthesis of the potent 5–HT1 receptor ligand, 5–carboxyamidotryptamine (5–CT)" Synthetic Communications, Bd. 23, Nr. 8, 1993, Seiten 1101–1110, XP000881512 in der Anmeldung erwaehnt.

Chengxi Yang et al.: "The use of Lewis acid in the reaction of zinc salts of indoles and acyl chloride" Synthetic Communications, Bd. 27, Nr. 12, 1997, Seiten 2125–2132, XP000881533.

* cited by examiner

Primary Examiner—Joseph K. McKane
Assistant Examiner—Golam M M Shameem
(74) Attorney, Agent, or Firm—Millen, White, Zelano & Branigan, P.C.

(57) ABSTRACT

A process for the preparation of a compound of formula (I)

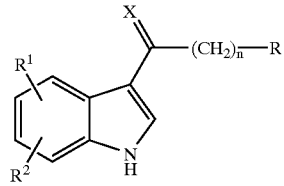

or a salt thereof in a Friedel-Crafts acylation catalyzed by a Lewis acid metal halide.

8 Claims, No Drawings

METHOD FOR PRODUCING 3-ALKANOYLINDOLES AND 3-ALKYLINDOLES

This application is a 371 of PCT/EP99/09334 filed Dec. 1, 1999.

The invention relates to a process for the preparation of compounds of the formula I.

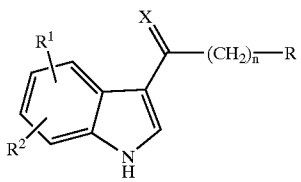

in which
R is Hal or methyl,
$R^1$, $R^2$ are in each case independently of one another H, A', aryl, $NH_2$, NHA", $N(A")_2$, COOA'", CN or Hal,
X is O or H,H,
A', A", A'" are in each case independently of one another alkyl having 1–6 carbon atoms,
Hal is F, Cl, Br or I and
n is 1, 2, 3, 4, 5 or 6,
and their acid addition salts, characterized in that
a) if X is O and R, $R^1$, $R^2$ and n are as defined above, a compound of the formula II

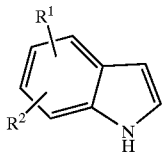

in which
$R^1$, $R^2$ are in each case independently of one another H, A', aryl, $NH_2$, NHA", $N(A")_2$, COOA'", CN or Hal.,
A', A", A'" are in each case independently of one another alkyl having 1–6 carbon atoms and
Hal is F, Cl, Br or I,
is reacted with a compound of the formula III

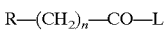
R—$(CH_2)_n$—CO—L      III in which
R is Hal or methyl,
L is Cl, Br, I, OH or a free OH group or an OH group which has been functionally modified to be reactive,
Hal is F, Cl, Br or I and
n is 1, 2, 3, 4, 5 or 6,
in a Friedel-Crafts acylation with catalysis of Lewis acid metal halides of the type R'—$Al(Cl)_2$,
in which
R' is A or aryl',
A is alkyl having 1–6 carbon atoms,
aryl' is unsubstituted phenyl or phenyl mono- or disubstituted by A', OA' or Hal,
Hal is F or Cl,
or
b) if X is H,H and R, $R^1$, $R^2$ and n are as defined above, a compound of the formula I in which X is O or R, $R^1$, $R^2$ and n are as defined above, is reduced using complex hydrides with activation by Lewis acid metal halides of the type R'—$Al(Cl)_2$,
in which
R' is A or aryl",
A is alkyl having 1–6 carbon atoms,
aryl' is unsubstituted phenyl or phenyl mono- or disubstituted by A', OA' or Hal,
Hal is F or Cl,
and/or in that a resulting base of the formula I is converted into one of its acid addition salts by treatment with an acid.

Processes for the preparation of acylated indoles are known, described, for example, by M. Tani et al., Chem. Pharm. Bull. 38 (12) 3261–3267 (1990), where the indole ring is substituted in the 2-position by ethoxycarbonyl.

A process for the preparation of methyl-3-(4-chloro-1-oxobutyl)-5-indolecarboxylate under $AlCl_3$ catalysis is described by Böttcher et al. in Liebigs Ann. Chem. 1988, 749–752.

In J. Med. Chem. 1980, 23, 1306–1310, an indole acylation via intermediate MgX salts of indole with R-CO-X is described by C. Gueremy.

In Tetrahedron Letters 28 (32), 3741–3744 (1987), an indole acylation via intermediate MgX salts is also described, by J. Bergmann et al.

Another acetylation 5-cyanoindole with acetyl chloride with catalysis of $SnCl_4$ is described by Agarwal et al. in Synthetic Communications 23 (8), 1101–1110 (1993).

The reduction of 4-indol-3-yl-4-oxobutyric acid using $LiAlH_4$ is described by J. S. L. Ibaceta-Lizana in J. Chem. Soc. Perkin Trans. II 1987, 1221–1226.

The reduction of a 3-alkanoylindole ester using $NaBH_4/BF_3$ ether is described by Böttcher et al. in Liebigs Ann. Chem. 1988, 749–752.

Another reduction of a phthalimide derivative of 3-acetyl-5-cyanoindole using $NaBH_4$ under isopropanol catalysis is described by Agarwal et al. in Synthetic Communications 23 (8), 1101–1110 (1993).

Surprisingly, investigations for the purposes of the synthesis of medicaments, which are described, for example, in DE 43 33 254 (EP 0 648 767), have shown that the compounds of the formula I can be obtained in at least comparable or higher yield compared with the prior art, the decisive advantages in this connection being the simple reaction which is carried out in homogeneous phase, and simple product isolation which is possible as a result.

As a consequence, this also means a lower consumption of solvent and energy.

For example, for the preparation of compounds of the formula I in which X is O, in the acylation according to step a), the catalyst, for example liquid isobutylaluminium dichloride (i-Bu-$AlCl_2$), can be introduced used and undiluted using a pump. The formation of virtually insoluble and nonstirrable solidS components, known from the prior art and often triggered under $AlCl_3$ catalysis, does not occur. Another advantage which can be mentioned is the appearance of fewer by-products since, for example, said i-Bu-$AlCl_2$ acts as a weaker Lewis acid than $AlCl_3$, and activation of a chloroalkyl function in the side chain and a Friedel-Crafts alkylation derived there from, as secondary reaction, is heavily suppressed.

Also in the reduction according to the invention as in step b) of the compounds of the formula I in which X is O, to give the compounds of the formula I in which X is H,H, advantages which can be mentioned are yields which are comparable to or higher than the prior art, coupled with the fact that the reaction is easier to carry out and the product is easier to isolate. A further advantage which can also be mentioned here is -he appearance of fewer by-products, particularly when reduction-sensitive substituents such as CN or ester groups are in positions 4 and 7 of the indole.

According to the process of the invention, the compound 3-(4-chlorobutanoyl)indole-5-carbonitrile is, for example, prepared in particular, which is then converted to the compound 1-[4-(5-cyanoindol-3-yl)butyl]-4-(2-carbamoylbenzofuran-5-yl)piperazine, disclosed in DE 43 33 254.

The invention therefore relates in particular to a process for the preparation of compounds of the formula I

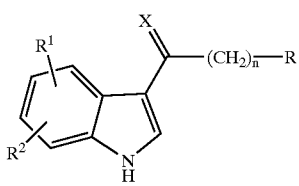

I in which
R is Hal,
$R^1$ is H,
$R^2$ is CN,
x is O or H,H,
Hal is F, Cl, Br or I and
n is 2, 3 or 4,
and their acid addition salts, characterized in that
a) if X is O and R, $R^1$, $R^2$ and n are as defined above, a compound of the formula II

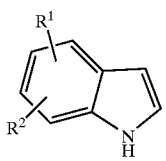

II in which
$R^1$ is H and
$R^2$ is CN,
is reacted with a compound of the formula III

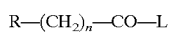 R—(CH$_2$)$_n$—CO—L      III in which
R is Hal,
L is Cl, Br, I, OH or a free OH group or an OH group which has been functionally modified to be reactive,
Hal is F, Cl, Br, I and
n is 2, 3 or 4,
in a Friedel-Crafts acylation with catalysis of Lewis acid metal halides of the type R'—Al(Cl)$_2$,
in which
R' is A,
A is alkyl having 1–6 carbon atoms,
or
b) if X is H,H and R, $R^1$, $R^2$ and n are as defined above, a compound of the formula I in which X is O and R, $R^1$, $R^2$ and n are as defined above, is reduced using complex hydrides with activation by Lewis acid metal halides of the type R'—Al(Cl)$_2$,
in which
R' is A,
A is alkyl having 1–6 carbon atoms,
and/or in that a resulting base of the formula I is converted into one of its acid addition salts by treatment with an acid.

The compounds of the formula I in which X is O and which are reduced in step b) can in principle also be obtained by customary processes by acylation under, for example, AlCl$_3$ catalysis. However, they are preferably prepared as in reaction step a) and then reduced as in step b).

The invention therefore preferably provides a process according to the two processes mentioned, for the preparation of compounds according to formula I in which X is H,H and R, $R^1$, $R^2$ and n are as defined above, characterized in that the compounds of the formula I in which X is O and R, $R^1$, $R^2$ and n are as defined above, are prepared as in step a) and then reduced as in step b)

A', A' and A''' are alkyl having 1, 2, 3, 4, 5 or 6 carbon atoms, preferably 1, 2, 3 or 4 carbon atoms, preference being given in particular to, for example, methyl or ethyl, but also propyl, isopropyl, and also butyl, isobutyl, sec-butyl or tert-butyl.

R in the compounds of the formulae I and III is preferably Cl or methyl.

In the compounds of the Lewis acid metal halides of the type R'—Al(Cl)$_2$, R' is preferably methyl, ethyl, propyl, isopropyl, butyl, tert-butyl, isobutyl, pentyl, neopentyl, isopentyl, phenyl, o-, m- or p-tolyl, o-, m- or p-methoxyphenyl, o-, m- or p-fluorine, o-, m- or p-chlorophenyl. Very particularly preferably, R' is isopropyl or isobutyl. The preferred compound isobutyl-Al(Cl)$_2$ is known, for example, from polymer chemistry.

In the compounds of the formulae I and II, aryl is unsubstituted phenyl or phenyl mono- or disubstituted by A, OA or Hal.

In the compounds of the formulae I and II, $R^1$ and $R^2$ are preferably in each case independently of one another H, methyl, ethyl, propyl, phenyl, amino, methylamino, ethylamino, dimethylamino, diethylamino, methoxycarbonyl, ethoxycarbonyl, cyanogen, fluorine or chlorine, and also carboxyl. Very particularly preferably, $R^1$ is H and $R^2$ is cyanogen.

In the compounds of the formulae I and III, n is preferably 2, 3 or 4, in particular 2 or 3.

The majority of the compounds of the-formulae II and III are known. In the compounds of the formula III, the radical L is preferably Cl or Br; it can, however, also be I, OH or an OH group which has been modified to become reactive, such as alkylsulphonyloxy having 1–6 carbon atoms (preferably methylsulphonyloxy) or arylsulphonyloxy having 6–10 carbon atoms (preferably phenyl-, p-tolylsulphonyloxy, 1- or 2-naphthalenesulphonyloxy). L can also be a suitable anhydride.

Furthermore, the -compounds of the formulae II and III are prepared by methods known per se, as are described in the literature (e.g. in the standard works such as Houben-Weyl, Methoden der organischen Chemie [Methods in Organic Chemistry], Georg-Thieme-Verlag, Stuttgart), under reaction conditions which are suitable and known for said reactions. In this connection, it is also possible to make use of variants which are known per se but which are not mentioned here.

The reaction of the compounds II and III proceeds in a suitable solvent. Suitable solvents are, for example, hydrocarbons, such as benzene, toluene, xylene; chlorinated hydrocarbons, such as, for example, dichloromethane; ketones such as acetone, butanone; ethers such as tetrahydrofuran (THF) or dioxane; amides such as dimethylformamide (DMF) or N-methylpyrrolidone; nitrites such as acetonitrile, and where appropriate also mixtures of these solvents with one another. The reaction time is between a few minutes and 14 days, depending on the conditions used, and the reaction temperature is between about 0° and 150°, normally between 0° and 60°.

The compounds of the formula I in which X is O are reduced using complex hydrides with activation by Lewis acids, in a suitable solvent. Suitable solvents are, for example, hydrocarbons, such as benzene, toluene, xylene; chlorinated hydrocarbons such as, for example, dichloromethane; ketones such as acetone, butanone; ethers such as tetrahydrofuran (THF) or dioxane; amides such as dimethylformamide (DMF) or N-methylpyrrolidone; nitrites such as acetonitrile, optionally also mixtures of these solvents with one another.

Preferred complex hydrides are compounds of the type MBH$_4$ where M=e.g. Na, Li, or 0.5 Ca.

The reaction time is between a few minutes and 14 days depending on the conditions used, and the reaction temperature is between about 0° and 150°, normally between 0° and 60°.

A base of the formula I can be converted into the corresponding acid addition salt using an acid, for example by reaction of equivalent amounts of the base and the acid in an inert solvent such as ethanol, and subsequent evaporation. Suitable acids for this reaction are, in particular, ones which produce physiologically acceptable salts. For example inorganic acids can be used, e.g. sulphuric acid, nitric acid, hydrohalic acid such as hydrochloric acid or hydrobromic acid, phosphoric acids such as orthophosphoric acid, sulphamic acid, and also organic acids, in particular aliphatic, alicyclic, araliphatic, aromatic or heterocyclic mono- or polybasic carboxylic, sulphonic or sulphuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesuiphonic acid, ethanedisulphonic acid, 2-hydroxyethanesulphonic acid, benzenesugphonic acid, p-toluenesudphonic acid, naphthalene-mono-and-disulphonic acids, laurylsulphuric acid. Salts with physiologically unacceptable acids, e.g. picrates, can be used to isola isolate and/or purify the compounds of the formula I.

All temperatures given above and below are in 0° C. In the examples below, "customary work-up," means: if necessary, adding water, if necessary adjusting the pH to between 2 and 10 depending on the constitution of the end product, extracting with ethyl acetate or dichloromethane, separating, drying the organic phase over sodium sulphate, evaporating and purifying by chromatography on silica gel and/or by crystallization.

EXAMPLE 1

Indole-5-carbonitrile→3-(4-chlorobutanoyl)indole-5-carbonitrile

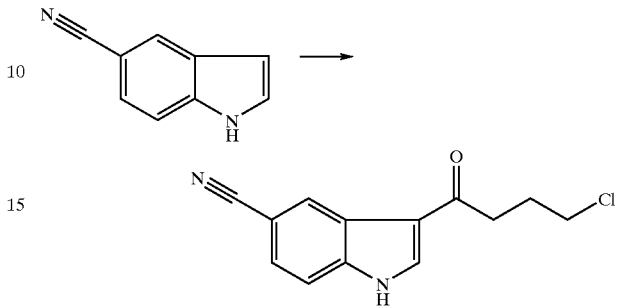

Description of the Experiment

Indole-5-carbonitrile (4800 g) is dissolved in dichloromethane (70 l) with stirring at 0–10° C. under nitrogen as protective gas, and Cl—(CH$_2$)$_3$COCl (6640 g) is added thereto. The T-controlled addition (0–10° C.) of isobutylaluminium dichloride (7300 g) then takes place. When acylation is complete (recognizable by chrom. analysis), the mixture is poured onto ice/water (64 kg) and the crystalline crude product 3-(4-chlorobutanoyl) indole-5-carbonitrile is separated off. For purification, the ketone is crystallized (6940 g/82%).

Indole-5-carbonitrile→3-(3-chloropropanoyl)indole-5-carbonitrile

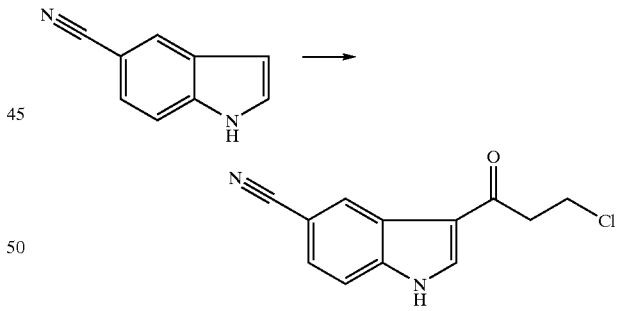

Description of the Experiment

Indole-5-carbonitrile (57.0 g) is dissolved in dichloromethane (790 g) with stirring at 0–10° C. under nitrogen as protective gas, and Cl—(CH$_2$)$_2$COCl (61 g) is added thereto. The T-controlled addition (0–10° C.) of isobutylaluminium dichloride (124 g) then takes place. When acylation is complete (recognizable by chrom. analysis), the mixture is poured onto ice/water, and the crystalline 3-(3-chloropropanoyl)indole-5-carbonitrile is separated off and dried under reduced pressure (ca. 83 g/89%).

EXAMPLE 2

3-(4-Chlorobutanoyl)indole-5-carbonitrile→3-(4-chlorobutyl)indole-5-carbonitrile

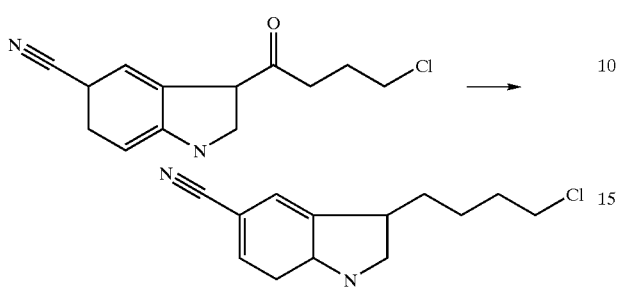

Description of the Experiment 3-(4-Chlorobutanoyl)indole-5-carbonitrile (75.5 9) is dissolved in dichloromethane (1980 g) with stirring at 0–10° C. under nitrogen as protective gas, and NaBH$_4$ (46.3 g) is added thereto. The T-controlled addition (0–10° C.) of isobutylaluminium dichloride (190 g) then takes place. When the reduction is complete (recognizable by chrom. analysis), the mixture is poured onto ice/water, and the crystalline product 3-(4-chlorobutyl)indole-5-carbonitrile is separated off as a uniform material (68 9; 95%).

3-(3-Chloropropanoyl)indole-5-carbonitrile→3-(3-chloropropyl)indole-5-carbonitrile

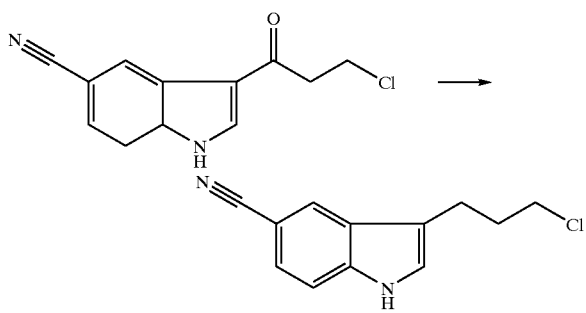

Description of the Experiment 3-(3-Chloropropanoyl)indole-5-carbonitrile (4.8 g) is dissolved in dichloromethane (224 g) with stirring at 0–10° C. under nitrogen as protective gas, and NaBH$_4$ (3.1 g) is added thereto. The T-controlled addition (0–10° C.) of isobutylaluminium dichloride (13 g) then takes place. When reduction is complete (recognizable by chrom. analysis), the mixture is poured onto ice/water, and the crystalline crude product 3-(3-chloropropyl)indole-5-carbonitrile is separated off and dried under reduced pressure. For purification, the indole is crystallized (3.9 g; 87%).

Comparative Experiment 1

3-(4-Chlorobutanoyl)indole-5-carbonitrile→3-(4-chlorobutyl)indole-5-carbonitrile

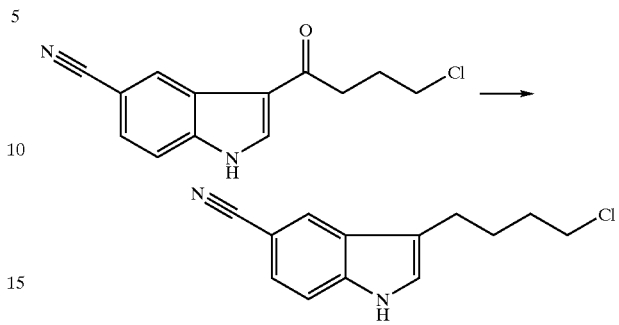

Description of the Experiment 3-(4-Chlorobutanoyl)indole-5-carbonitrile (75.5 g) is dissolved in dichloromethane (1980 g) with stirring at 0–10° C. under nitrogen as protective gas, and LiAlH$_4$ (46 g) is added thereto. After the usual reaction time and work-up, it was not possible to isolate a product.

Comparative Experiment 2

3-(4-Chlorobutanoyl)indole-5-carbonitrile→3-(4-chlorobutyl)indole-5-carbonitrile

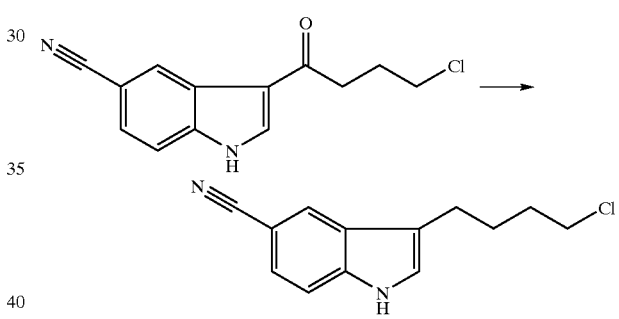

Description of the Experiment 3-(4-Chlorobutanoyl)indole-5-carbonitrile (75.5 g) is dissolved in dichloromethane (1980 g) with stirring at 0–10° C. under nitrogen as protective gas, and NaBH$_4$/BF$_3$ ether is added thereto. After the usual reaction time and work-up, it was not possible to isolate a product.

What is claimed is:

1. A process for the preparation of a compound of formula

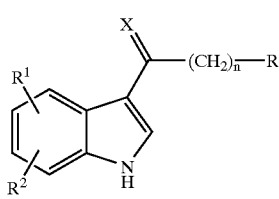

I in which

R is Hal or methyl,

R$^1$, R$^2$ are, each independently, H, A', aryl, NH$_2$, NHA", N(A")$_2$, COOA''', CN or Hal, X is O or H,H, A', A", A''' are, each independently, alkyl having 1–6 carbon atoms, Hal is F, Cl, Br or I, and n is 1, 2, 3, 4, 5 or 6, or an acid addition salt thereof, comprising a) if X is O, reacting a compound of formula II

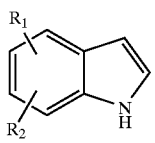

in which

R¹, R² are, each independently, H, A', aryl, NH₂, NHA'', N(A'')₂, COOA'', CN or Hal, A', A'', A''' are, each independently, alkyl having 1–6 carbon atoms, and Hal is F, Cl, Br or I, with a compound of formula III

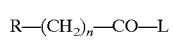

in which

R is Hal or methyl,

L is Cl, Br, I, OH, a free OH group or an OH group which has been functionally modified to be reactive, Hal is F, Cl, Br or I, and n is 1, 2, 3, 4, 5 or 6, in a Friedel-Crafts acylation catalyzed by a Lewis acid metal halide of formula

in which

R' is A or aryl',

A is alkyl having 1–6 carbon atoms, aryl' is unsubstituted phenyl or phenyl mono- or disubstituted by A', OA' or Hal, Hal is F or Cl, or b) if X is H,H, reducing a compound of formula I in which X is O, by a complex hydride, wherein said reduction is catalyzed by a Lewis acid metal halide of formula

in which

R' is A or aryl',

A is alkyl having 1–6 carbon atoms, aryl' is unsubstituted phenyl or phenyl mono- or disubstituted by A', OA' or Hal, Hal is F or Cl, or converting a base of formula I into an acid addition salt by reacting said base with an acid.

2. A process for the preparation of a compound of formula

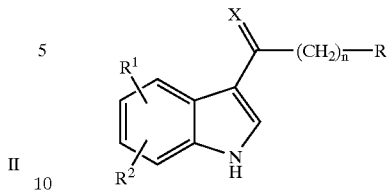

in which

R is Hal,

R¹ is H,

R² is CN,

X is O or H,H,

Hal is F, Cl, Br or I, and n is 2, 3 or 4, or an acid addition salt thereof, comprising a) if X is O, reacting a compound of formula II

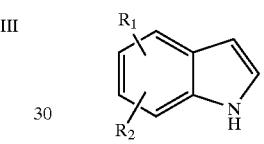

in which

R¹ is H, and

R² is CN, with a compound of formula III

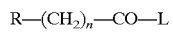

in which

R is Hal,

L is Cl, Br, I, OH, a free OH group or an OH group which has been functionally modified to be reactive, Hal is F, Cl, Br or I, and n is 2, 3 or 4, in a Friedel-Crafts acylation catalyzed by a Lewis acid metal halide of formula

in which

R' is A,

A is alkyl having 1–6 carbon atoms, or b) if X is H,H, reducing a compound of formula I in which X is O, by a complex hydride, wherein said reduction is catalyzed by a Lewis acid metal halide of formula R'—Al(Cl)₂, in which R' is A, A is alkyl having 1–6 carbon atoms, or converting a base of formula I into an acid addition salt by reacting said base with an acid.

3. A process according to claim 1, wherein in process b), the compound of formula I in which X is O is prepared according to process a).

4. A process according to claim 2, wherein in process b), the compound of formula I in which X is O is prepared according to process a).

5. A process according to claim 1, wherein the complex hydride is of formula $$MBH_4$$

in which

M is Na, Li or 0.5 Ca.

6. A process according to claim 2, wherein the complex hydride is of formula $$MBH_4$$

in which

M is Na, Li or 0.5 Ca.

7. A process according to claim 1, wherein the Lewis acid metal halide is isobutylaluminium dichloride.

8. A process according to claim 2, wherein the Lewis acid metal halide is isobutylaluminium dichloride.

* * * * *